(12) United States Patent
Voegelin et al.

(10) Patent No.: US 9,778,277 B2
(45) Date of Patent: Oct. 3, 2017

(54) PROCESS AND APPARATUS FOR TESTING SUBSTANCES FOR POTENTIAL CARCINOGENICITY

(75) Inventors: Dieter Voegelin, Sissach (CH); Patrick Iaiza, Saint Louis (FR); Thomas Zumstein, Weil am Rhein (DE); Tom Kissling, Riehen (CH)

(73) Assignee: F. Hoffmann-La Roche AG, Basel (CH)

( * ) Notice: Subject to any disclaimer, the term of this patent is extended or adjusted under 35 U.S.C. 154(b) by 618 days.

(21) Appl. No.: 13/254,941

(22) PCT Filed: Mar. 19, 2010

(86) PCT No.: PCT/EP2010/053605
§ 371 (c)(1),
(2), (4) Date: Sep. 6, 2011

(87) PCT Pub. No.: WO2010/106162
PCT Pub. Date: Sep. 23, 2010

(65) Prior Publication Data
US 2012/0149058 A1   Jun. 14, 2012

(30) Foreign Application Priority Data
Mar. 20, 2009   (EP) ..................... 09155692

(51) Int. Cl.
*C12M 1/34* (2006.01)
*C12Q 1/06* (2006.01)
(Continued)

(52) U.S. Cl.
CPC ....... *G01N 35/1067* (2013.01); *G01N 35/028* (2013.01)

(58) Field of Classification Search
CPC .................. G01N 35/1067; G01N 35/028
(Continued)

(56) References Cited

U.S. PATENT DOCUMENTS 3,484,206 A * 12/1969 Loebl ............................. 422/64
3,844,896 A * 10/1974 Sharpe ....................... 435/286.4
(Continued)

FOREIGN PATENT DOCUMENTS

EP   0206945 A2 * 12/1986 .............. B01L 3/021
GB   1372847 A    11/1974
(Continued)

OTHER PUBLICATIONS

Bernd Traupe "Automatisierte Mikrobiologie: identifizierund von antimikrobiellen Substanzen fur Kosmetika" English language tanslation.*

(Continued)

*Primary Examiner* — Michael Hobbs
*Assistant Examiner* — Liban Hassan
(74) *Attorney, Agent, or Firm* — Mintz Levin Cohn Ferris Glovsky and Popeo, P.C.

(57) ABSTRACT

An apparatus (2) for the automatic testing of substances for carcinogenicity comprises: a plate support (3) on which at least one micro-well plate (1) can be placed; a movable pipetting unit (4) comprising a predetermined number of pipettes (40); a number of containers (5) containing a liquid culture medium (50), the number of containers (5) corresponding to the number of pipettes (40) of the pipetting unit (4); a dish support (6) on which a corresponding number of dishes (60) can be placed, each having a bottom and an upstanding side wall (601); a plurality of spinners (63) for spinning the dishes (60); a plurality of suction cups (62) for placing a lid (600) on each of the dishes; and a plurality of laterally arranged belts (64,65) for transporting the closed dishes (60) to an intermediate storage (8).

5 Claims, 7 Drawing Sheets

(51) Int. Cl.
*G01N 35/10* (2006.01)
*G01N 35/02* (2006.01)

(58) Field of Classification Search
USPC .................................. 435/287.3, 39, 287.1
See application file for complete search history.

(56) References Cited

U.S. PATENT DOCUMENTS

| | | | |
|---|---|---|---|
| 5,869,258 | A | 2/1999 | Gee et al. |
| 6,325,114 | B1* | 12/2001 | Bevirt et al. ................... 141/130 |
| 2004/0106145 | A1* | 6/2004 | Gold et al. ......................... 435/6 |
| 2006/0073491 | A1 | 4/2006 | Joseph et al. ..................... 435/6 |
| 2006/0081539 | A1* | 4/2006 | Safar et al. ..................... 210/695 |
| 2007/0003445 | A1* | 1/2007 | Belgardt et al. ............... 422/100 |

FOREIGN PATENT DOCUMENTS

| | | |
|---|---|---|
| JP | 2001-153761 | 6/2001 |
| JP | 2001-218576 | 8/2001 |
| JP | 2002-098704 | 4/2002 |
| JP | 2005-091339 | 4/2005 |

OTHER PUBLICATIONS

Lamaziere Jacques, "English language translation of EP0206945A2", translated on Jun. 26, 2016.*
Bernd Traupe: "Automatisierte Mikrobiologie: Identifizierund von antimikrobiellen Substanzen fur Kosmetika.", Tecan Journal [online], vol. 1, 2004, pp. 7-8.
International Search Report for PCT/EP2010/053605 dated May 6, 2010.
European Search Report for European Patent Application No. 09155692.8 dated May 7, 2009.
A Summary of Major Test Methods for Toxicity and Safety Testing (online), from the website of Sumika Chemical Analysis Service, Ltd. (retrieved on Jul. 10, 2014), http://www.scas.co.jp/substance/03_1.html; English Abstract.
English Abstract of JP-2002-098704.
English Abstract of JP-2005-091339.
English Abstract of JP-2001-153761.
English Abstract of JP-2001-218576.

* cited by examiner

PROCESS AND APPARATUS FOR TESTING SUBSTANCES FOR POTENTIAL CARCINOGENICITY

CROSS-REFERENCE TO RELATED APPLICATIONS

This application is a national phase of International Application No. PCT/EP2010/053605, filed on Mar. 19, 2010, which claims priority to European Patent Application No. 09155692.8, filed on Mar. 20, 2009. The contents of all of these applications are expressly incorporated herein by reference in their entireties.

BACKGROUND OF THE INVENTION

The present invention relates to a process and an apparatus for testing substances for potential toxicity.

During the drug discovery process a variety of tests are performed to avoid investments in further testing or development of substances which are likely to not be able to fulfil regulatory requirements, e.g. such substances may turn out to be toxic or otherwise be not suitable for the development of a drug. One of these test in a very early phase of the drug discovery process is the so-called "Ames test".

In essence, the Ames test is a test for determining if a substance is mutagenic and is based on the assumption that a substance that is mutagenic (for the bacteria used in the Ames-test) may also turn out to be carcinogenic.

Although, in fact, some substances that cause cancer do not give a positive Ames test (and vice versa), the simplicity and low cost of this test makes it highly recommendable in the process of screening substance for possible carcinogenicity.

The respective bacteria (strains of *salmonella*) used in the Ames test carry a defective (mutant) gene making them unable to synthesize the amino acid histidine from the ingredients in the culture medium, thus making them unable to grow on a culture medium lacking histidine. However, some types of mutations can be reversed (back mutation), with the gene regaining its function. These revertants are then able to grow on a culture medium lacking histidine.

Many substances are not mutagenic (or carcinogenic) themselves but become converted into mutagens (or carcinogens) as they are metabolized by the body. This is the reason why the Ames test also includes liver enzymes. In case there is bacterial growth on the culture medium lacking histidine without liver enzymes having been added then the substance itself is mutagenic. If no such bacterial growth occurs without liver enzymes having been added but occurs with liver enzymes having been added then the metabolite of this substance is mutagenic. In either case, the substance is not further considered in further testing or in development of a drug. As already mentioned, the Ames test is routinely used in the drug discovery process due to its simplicity, low cost and its high probability that a substance (or its metabolite) which is marked by the Ames test as being cancerogenic is in fact cancerogenic. In addition, in some countries having performed the Ames test is a regulatory requirement that must be complied with in order to later on get the allowance for a drug to enter into the market.

For the reasons mentioned above, the Ames test is a well-established test in the drug discovery process. However, since nowadays very large numbers of substances are synthesized automatically in only small amounts the tests have to be performed in a highly efficient manner and with these small amounts of the substances. Typically these substances are provided in various differently diluted concentrations in micro-well plates (e.g. in micro-well plates having 96 micro-wells). However, the testing of these substances—or at least some essential steps thereof—is still performed manually to a large extent.

SUMMARY OF THE EMBODIMENTS

There is therefore a need for a process and an apparatus for efficiently and automatically performing the Ames test, and preferably the process and apparatus should be suitable to use standard laboratory equipment such as micro-well plates, Petri-dishes, standard pipettes, etc., so that in view of the large numbers of substances to be tested with different concentrations the efficiency of the Ames test can be substantially increased. Also, only small amounts of the substances to be tested should be necessary.

To achieve this, the present invention suggests a process as is it specified by the features of the independent claim directed to a process. Further embodiments of the process according to the invention are the subject of the dependent process claims.

In accordance with the present invention the process for automatically testing substances for potential carcinogenicity comprises the steps of:

providing a plurality of substance/*salmonella* mixtures in the wells of a micro-well plate;

moving a predetermined number of pipettes towards the wells of the micro-well plate;

intaking into the pipettes a desired amount of the respective substance/*salmonella* mixtures contained in the wells of the micro-well plates;

moving the pipettes with the intaken substance/*salmonella* mixtures to a corresponding number of containers containing a liquid culture medium;

intaking into the pipettes a desired amount of liquid culture medium and mixing it with the respective intaken substance/*salmonella* mixtures;

moving the pipettes with the intaken substance/*salmonella* mixtures and culture medium to a corresponding number of dishes, each dish having a bottom and an upstanding side wall surrounding the bottom as well as a solid culture medium arranged on the bottom of the dish;

dispensing the respective mixtures of substance/*salmonella* and culture medium from the pipettes into the associated dishes;

spinning the dishes to effect spin-coating of the solid culture medium in the respective dish with the mixture of substance/*salmonella* and liquid culture medium dispensed into the said dish;

stopping spinning of the dishes to allow the dispensed mixture to form a uniform layer of substance/*salmonella* and liquid culture medium on the entire surface of the solid culture medium in the respective dish;

closing the dishes with respective lids;

incubating the closed dishes for a predetermined time under predetermined conditions; and counting the number of *salmonella* colonies in the dishes so as to determine whether or not the substance is potentially cancerogenic.

This process is particularly suitable to automatically perform the Ames test and increase the efficiency of performing the test, since the automatically performed Ames test allows to process a large number of substance/*salmonella* mixtures in a comparatively short time. Also, it is possible to use standard laboratory equipment such as e.g. standard 96 well micro-well plates, in the wells of which only small amounts of the substance/*salmonella* mixtures to be tested can be provided with the substance being contained in the mixtures in different concentrations. In addition, while not being mandatory it is possible to use standard Petri-dishes in which a disk of a solid culture medium such as Agar is arranged. The spin-coating of the solid culture medium (Agar) in the dishes, which is achieved by first spinning the dishes after the substance/*salmonella* mixture has been dispensed on the solid culture medium and then stopping the spinning of the dishes, results in a uniform layer of mixture on the solid culture medium. After having closed the dishes with a lid and after a predetermined incubation time counting of the number of *salmonella* colonies can be performed easily and reliably.

In one variant of the process according to the invention, the step of providing a plurality of substance/*salmonella* mixtures to be tested in the wells of a micro-well plate comprises:

preparing a predetermined number of different dilutions of each substance to be tested;

filling the different dilutions of the substances into different wells of the micro-well plate;

admixing *salmonella* strains to the different dilutions of the respective substance to obtain substance/*salmonella* mixtures containing the substance to be tested in different dilutions; and providing these different dilutions of the substance/*salmonella* mixtures in different wells of the micro-well plate.

This variant is advantageous in that the substances to be tested in different concentrations in form of respective substance/*salmonella* mixtures in different wells preferably of one and the same micro-well plate can be prepared at a location remote from the location where the micro-well plates are provided for the automatic processing. Once an entire micro-well plate has been prepared, it is either forwarded directly to the location where the plates can be automatically processed, or it is stored in an intermediate storage from where it can be automatically forwarded for processing.

In a further embodiment of this variant of the process according to the invention, the step of providing a plurality of substance/*salmonella* mixtures further comprises adding liver enzymes in a liquid form to the different dilutions of each substance prior to admixing the *salmonella* strains. This embodiment of the process is advantageous in that in addition to performing the Ames-test for the substances per se (or the respective substance/*salmonella* mixture) the Ames-test is also performed for potential metabolites of the substances (which are obtained with the aid of the liver enzymes), so that both the substances per se and potential metabolites thereof are automatically subjected to the Ames-test. Alternatively, a buffer liquid can be added instead of the liver enzymes if appropriate, however, in this case it is the substance itself rather than any metabolite thereof which is subjected to the Ames-test.

In a further variant of the process according to the invention, the respective solid culture medium arranged in the respective dish is heated prior to dispensing the mixtures of substance/*salmonella* and culture medium from the pipettes into the associated dishes. This pre-heating increases the hydrophilicity of the solid culture medium (e.g. Agar) arranged in the respective dish and thus further improves the uniform formation of the layer of the dispensed substance/*salmonella* mixture. By way of example, the heating of the solid culture medium arranged in the respective dish can be performed using IR-radiation (InfraRed).

In a further variant of the process according to the invention, the step of intaking into the pipettes a desired amount of liquid culture medium and mixing it with the respective intaken substance/*salmonella* mixtures comprises aspirating air into the pipettes for performing the mixing of the intaken substance/*salmonella* mixtures with the liquid culture medium. Through the aspiration of air a good mixing of the substance/*salmonella* mixture with the liquid culture medium (e.g. Soft Agar) is achieved.

As regards the apparatus for the automatic testing of substances for potential carcinogenicity according to the invention, this apparatus comprises:

a plate support on which at least one micro-well plate can be placed, the micro-well plate comprising a plurality of substance/*salmonella* mixtures or substance/*salmonella*/liver enzymes mixtures in the respective wells of the plate;

a movable pipetting unit comprising a predetermined number of pipettes;

a number of containers containing a liquid culture medium, the number of containers corresponding to the number of pipettes of the pipetting unit;

a dish support on which a corresponding number of dishes can be placed, each dish having a bottom and an upstanding side wall surrounding the bottom as well as a solid culture medium arranged on the bottom of the dish;

spinning means for spinning the dishes;

closing means for placing a lid on each of the dishes so as to close the respective dishes;

transport means for transporting the closed dishes to an intermediate storage capable of collecting a plurality of closed dishes so as to forward them to an incubator.

Such apparatus allows to automatically perform large numbers of Ames-tests in a comparatively short time using standard laboratory equipment such as e.g. standard 96 well micro-well plates, in the wells of which only small amounts of the substances to be tested can be provided in different concentrations with or without liver enzymes. The micro-well plates are provided on a plate support arranged at a well-defined location, so that different 96 well micro-well plates are always provided at the same location. The movable pipetting unit can be automatically moved to the location of the plate support where the micro-well plate with its 96 different wells is provided. The pipetting unit comprises a predetermined number of pipettes and is capable of automatically intaking from a corresponding number of wells a corresponding number of substance/*salmonella* mixtures or substance/*salmonella*/liver enzymes mixtures, respectively, and then moves the pipettes towards a corresponding number of containers each containing a liquid culture medium (e.g. Soft Agar). The pipetting unit then aspirates a predetermined amount of liquid culture medium and a mixture with the intaken substance/*salmonella* mixture or with the intaken substance/*salmonella*/liver enzymes mixtures is produced. After the intake of culture medium movable pipetting unit moves on to a dish support where a corresponding number of dishes (e.g. Petri-dishes) each containing a disk of a solid culture medium (e.g. Agar) arranged on the bottom of the dish is waiting. The mixtures contained in the pipettes are then dispensed into a respective spinning dish. The centrifugal forces acting on the respective dispensed liquid mixture forces the said mixture towards the upstanding side wall surrounding the bottom of the dish. Spinning is then stopped allowing the liquid mixture to evenly distribute over the solid culture medium so as to form a uniformly distributed film. Once this film has been formed, the closing unit places a lid on the dish and the closed dishes are then transported towards the intermediate storage, where a plurality of such dishes can be stored. Once the intermediate storage is complete, it can be forwarded to an incubator. After a predetermined incubation time counting of the number of *salmonella* colonies can be easily and reliably performed.

One embodiment of the apparatus according to the invention further comprises heating means which are capable of being positioned above the respective solid culture medium arranged in the respective dishes on the dish support. As already mentioned above, these heating means can be used to temporarily heat the solid culture medium (e.g. Agar) so as to increase the hydrophilicity thereof. In a particular embodiment of this apparatus, the heating means comprise a number of IR-heaters corresponding to the number of dishes that can be arranged on the dish support at the same time.

In a further embodiment of the apparatus according to the invention, the pipettes of the pipetting unit are arranged at an inclination angle relative to a normal to the plane of the plate support, with adjacently arranged pipettes being arranged at opposite inclinations relative to the normal. This embodiment is particularly advantageous when using standard micro-well plates such as the afore-mentioned 96 well micro-well plates in connection with standard pipette tips, e.g. 5 ml (or even larger) standard pipette tips, which—while having a tip with a very small diameter—conically increase in diameter. Due to the small spatial distance of adjacent wells of such micro-well plates it is then not possible to arrange these standard pipettes normal to the plane of the plate support if the pipette tips are to be introduced in adjacently arranged wells of such micro-well plates since in this case adjacently arranged pipettes would collide. However, in case adjacent standard pipette tips are arranged inclined relative to the normal to the plane of the plate support at opposite inclinations (e.g. one pipette tip is arranged inclined at a positive angle relative to the normal while the adjacent one is inclined at a negative angle relative to the normal, and so on) then it is possible to use standard pipette tips and 96 well micro-well plates and at the same time it is possible to introduce adjacently arranged pipette tips into adjacently arranged wells of the micro-well plate without collision. The angle of inclincation may be in the range of up to 10° relative to the normal, and amounts in particular about 7.5° relative to the normal.

In a further embodiment of the apparatus according to the invention the pipetting unit comprises spacing means for laterally moving the pipettes towards and away from one another. These spacing means allow the pipettes to be arranged very closely relative to one another at the location where they intake the substance/*salmonella* mixtures or substance/*salmonella*/liver enzymes mixtures from adjacent wells of the micro-well plate, and to then move them away from one another so that they can subsequently be introduced into the containers containing the liquid culture medium (e.g. Soft Agar). Once this has been performed they can be moved either farther away from one another or closer to one another, depending on the spatial distance between the centres of the dishes on the dish support. In one particular variant of this embodiment of the apparatus the spacing means comprise a gear with a fixed gear transmission ratio, which may be such that the ratio of the distances between adjacent pipettes always remains constant. This is an embodiment which is simple from a technical point of view.

According to a further embodiment of the apparatus according to the invention the pipettes are disposable pipettes. This is advantageous in that the respective pipettes can be used only once so that no cross-contamination or mixing of substances may occur.

BRIEF DESCRIPTION OF THE DRAWINGS

Further advantageous aspects of the invention become evident from the following description of an embodiment of the invention in which.

DETAILED DESCRIPTION OF THE INVENTION

Figure 1:
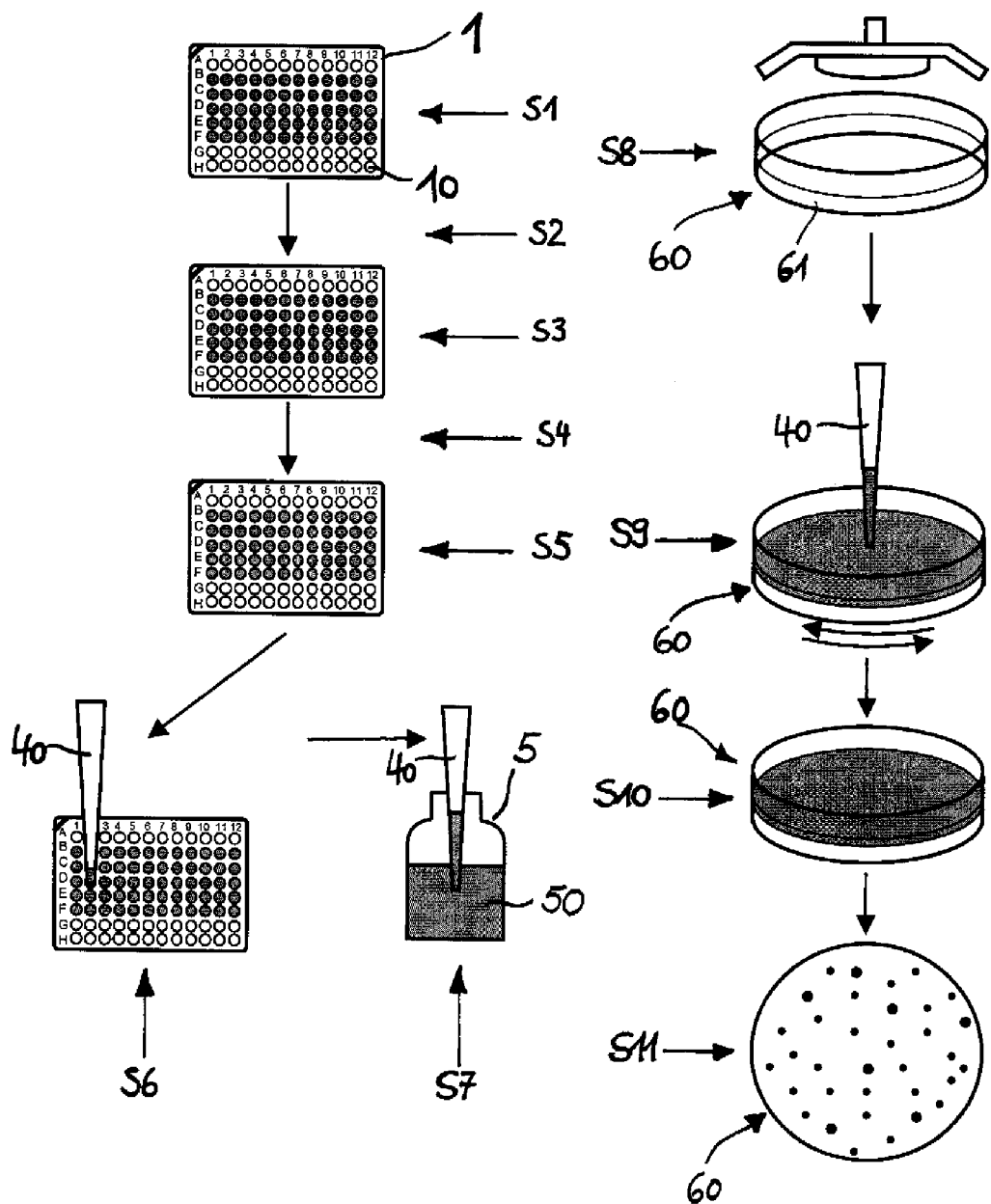
FIG. 1 shows a schematic illustration of essential steps of one variant of the process according to the invention.

In FIG. 1 some essential steps of the process according to the invention are shown. A standard 96 well micro-plate 1 is shown of which only sixty wells arranged in five rows and twelve columns are used in this embodiment. However, this is only due to the fact that the corresponding embodiment of the apparatus described in detail herein further below is equipped with a corresponding number of five pipettes. It is of course possible to use another number of rows of the micro-well plate 1, and in particular it is possible to use all 96 wells of such standard micro-well plate 1 and to provide a corresponding number of eight pipettes in the apparatus.

In a first step S1, the different substance or compound dilutions are prepared and introduced into the wells 10 of the micro-well plate 1. This can be done manually and remote from the apparatus according to the invention, but can also be done in the interior of the outer housing of the apparatus.

The next step S2 will be performed only if it is not the substance or compound per se but rather any potential metabolites thereof which is to be tested. This step S2 comprises the dispensing of a predetermined amount of a liver enzymes mixture into the respective wells 10 of the micro-well plate 1. If the substance per se is to be tested, it is also possible to dispense a predetermined amount of a buffer solution into the respective wells 10 of micro-plate 1.

The next step S3 is capturing and analyzing a picture of the substances or compounds (or their mixtures with liver enzymes or buffer solution, respectively) contained in the wells 10 of the micro-well plate 1. In case a substance or compound precipitates it cannot be absorbed by the bacteria strains, this can only happen when the substance or compound is in solution. Therefore, in case precipitation occurs, the substances contained therein cannot be tested.

The next step S4 comprises dispensing a predetermined amount of a bacteria solution, such as e.g. a solution containing *salmonella* strains, into the respective wells 10 of the micro-well plate 1.

In a step S5, the so prepared micro-well plate 1 containing in its wells 10 the substance/*salmonella* mixtures (or the respective substance/*salmonella*/liver enzymes mixture) is then incubated for a predetermined amount of time under predetermined conditions (and is optionally shaken during that time). Thereafter, the substance/*salmonella* mixtures (or the respective substance/*salmonella*/liver enzymes mixtures) are ready to be subjected to the automatic Ames-test with the aid of the apparatus according to the invention, an embodiment of which will be explained further below.

In the next step S6, a number of pipettes 40—in the embodiment described five pipettes—of which only one pipette 40 is shown in FIG. 1, is moved towards the wells 10 of micro-well plate 1. A desired amount of the substance/*salmonella* mixtures contained in the wells is then intaken into the respective pipettes 40 by aspiration.

In the next step S7, the pipettes 40 with the intaken substance/*salmonella* mixtures are moved to a corresponding number of containers where a desired amount of a liquid culture medium 50, such as e.g. a warm Soft Agar solution, is intaken into the pipettes 40 by aspiration. Also, some air may be aspirated, too, so as to achieve a good mixing of the substance/*salmonella* mixture with the liquid culture medium. The pipettes 40 with the substance/*salmonella*/culture medium mixture is then moved to a corresponding number of dishes 60, in this embodiment five dishes of which only one dish 60 is shown in FIG. 1.

The dishes 60 contain a substantially solid culture medium, such as an Agar disk 61, arranged on the bottom of the respective dish. The dishes 60 in the embodiment described are standard Petri-dishes. Shortly before the dispensing of the mixtures contained in the pipettes 40 into the respective dishes 60, the Agar disks 61 are heated in step S8 with the aid of an IR-radiator so as to increase the hydrophilicity of the Agar disks.

Thereafter, in step S9 the mixture contained in the pipettes 40 is centrally dispensed into the respective dishes 60. The Petri-dishes are then spun either clock-wise or counterclockwise as is indicated by the arrows so as to coat the solid Agar disk 61 with the dispensed mixture. Spinning is then stopped allowing a uniform film to form on the solid Agar disk 61.

In step S10 a lid is placed onto the Petri-dishes and the Petri-dishes are then incubated for a predetermined amount of time and under predetermined conditions. After that, in step S11 the number of *salmonella* colonies that have developed is counted in each Petri-dish 60. If no colonies have developed or if only a number of colonies has developed which is lower than a predetermined threshold number, the substance or its metabolite, respectively, has passed the Ames-test.

Figure 2:
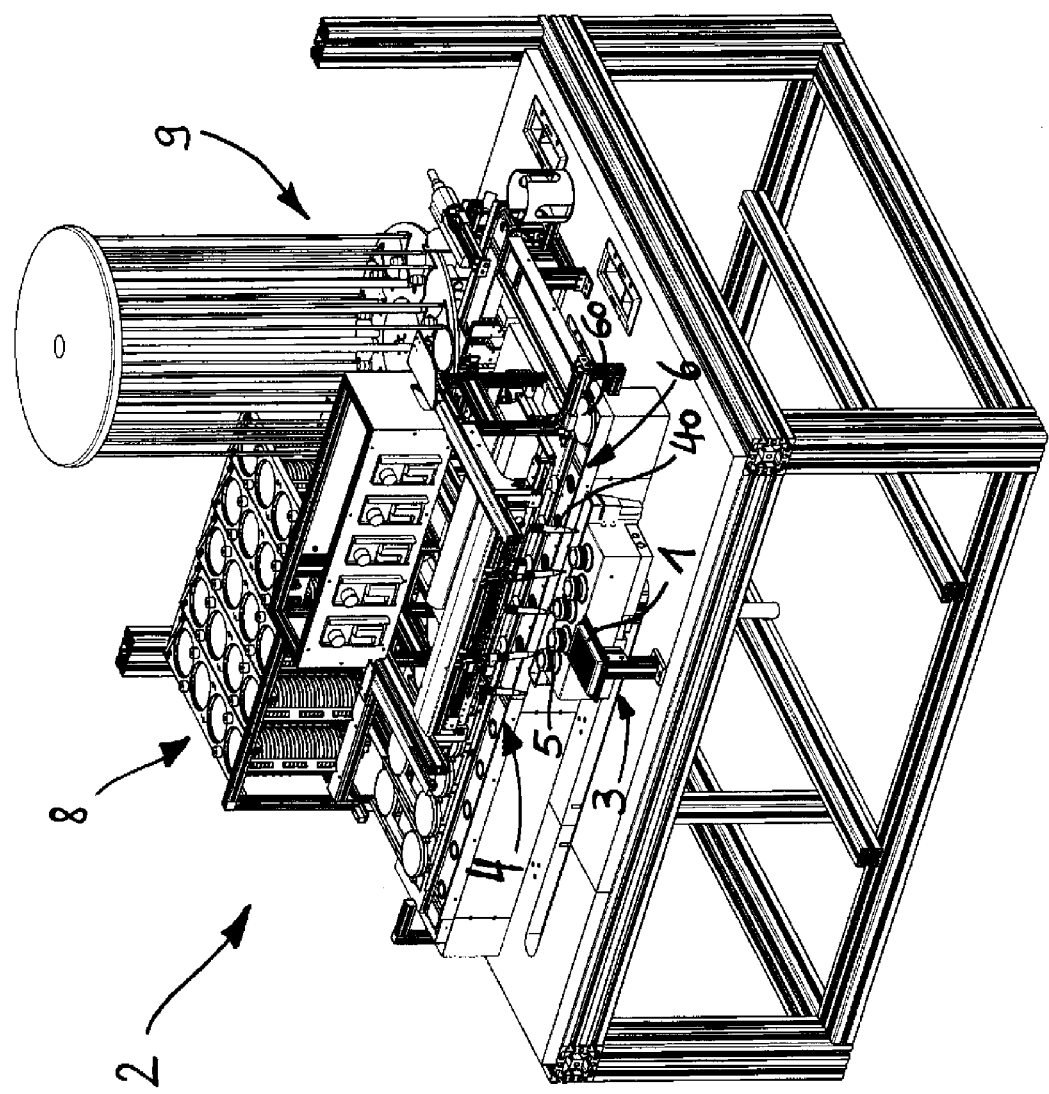
FIG. 2 shows a perspective view of an embodiment of the apparatus according to the invention.

FIG. 2 shows an embodiment of an apparatus 2 according to the invention in a perspective view (without outer housing). Apparatus 2 comprises a plate support 3 on which a micro-well plate 1 can be placed, a movable pipetting unit 4, comprising a predetermined number—in this embodiment five—pipettes 40, a corresponding number of containers 5 each containing a liquid culture medium 50 (see FIG. 1) such as Soft Agar, and a dish support 6 on which five Perti-dishes 60 can be placed. Also, an intermediate storage 8 for the Petri-dishes as well as a magazine 9 in form of a cylindrical carousel for providing unused Petri-dishes can be seen in FIG. 2.

Figure 3:
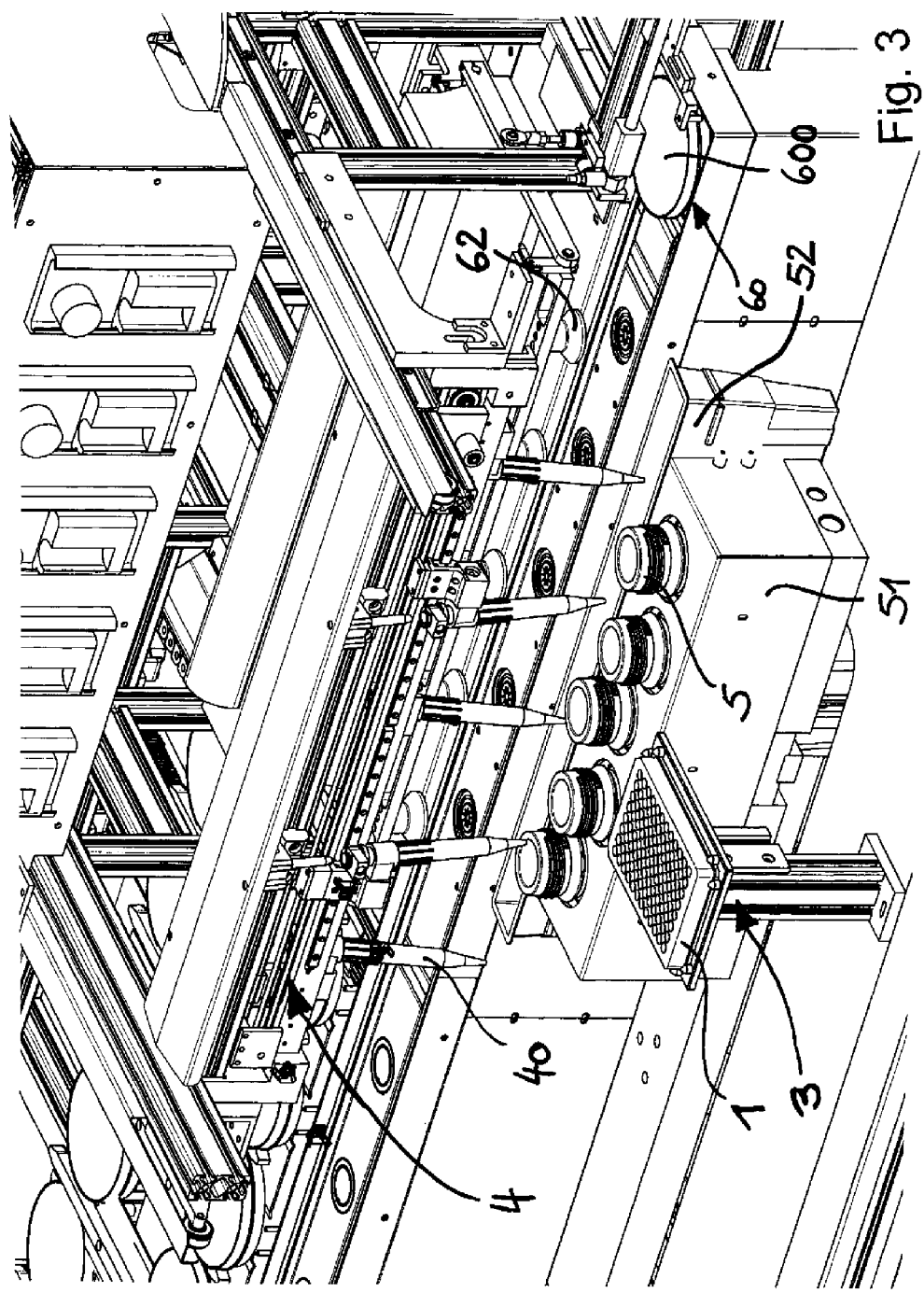
FIG. 3 shows a detail of the embodiment of the apparatus of FIG. 2 with the pipettes being arranged near the containers containing the liquid culture medium.

FIG. 3 shows a detail of the embodiment of the apparatus 2 of FIG. 2 with the pipettes 40 of pipetting unit 4 being arranged near the containers 5 containing the liquid culture medium. The containers 5 are arranged in a housing 51 to which a pan 52 is attached for collecting used pipettes 40, as will be described further below. From FIG. 3 a number of suction cups 62 can be seen which will be lowered once each of the Petri-dishes 60 has reached its position on the respective drive 63 for spinning the Petri-dish 60. As can be seen in FIG. 3 at the lower right end, the Petri-dishes 60 are provided with their lids 600 being closed. The dishes 60 are moved to their position on the respective drive 63 whereupon suction cups 62 are lowered to the respective lids 600 and suction is applied. Suction cups 62 are then lifted again with the respective lids 600 being attached to them so as to expose the Agar disk 61 (see FIG. 1) arranged on the bottom of the Petri-dish 60 (without lid).

Figure 4:
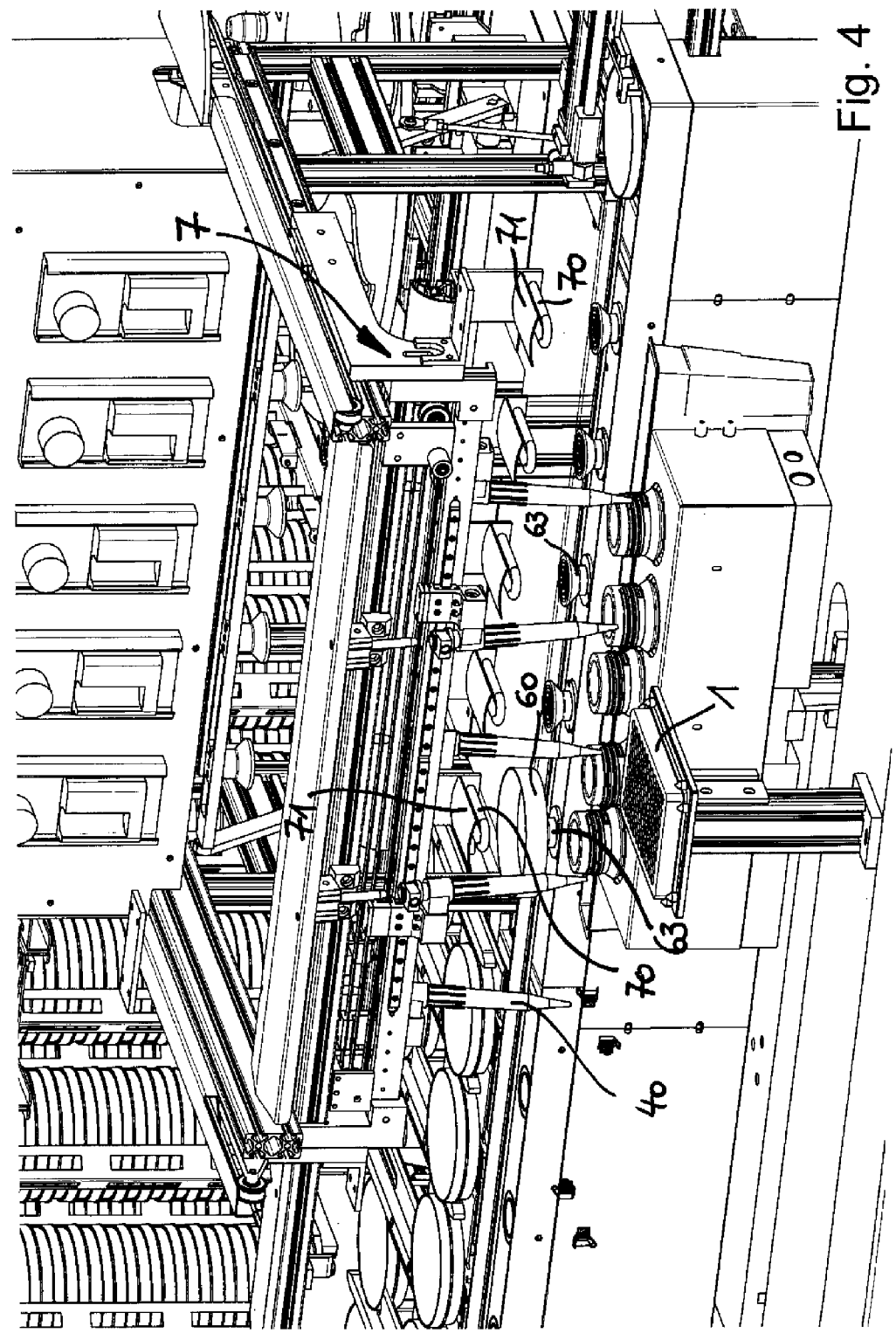
FIG. 4 shows a detail of the embodiment of the apparatus of FIG. 2 showing the IR-heaters in their position above the dishes in the dish support.

In FIG. 4 one Petri-dish 60 without lid is shown on its respective drive 63 with the drive being in a lifted position. A heating unit 7 comprising a number of IR-heaters 70 with reflectors 71, corresponding to the possible number of Petri-dishes 60 on the dish support 6 has been moved to a position where the IR-heaters 70 are arranged above the open dishes. The IR-heaters 70 then irradiate the respective Agar disks with IR-radiation so as to increase their hydrophilicity. Thereafter, the heating unit 7 is moved away towards the rear.

Figure 5:
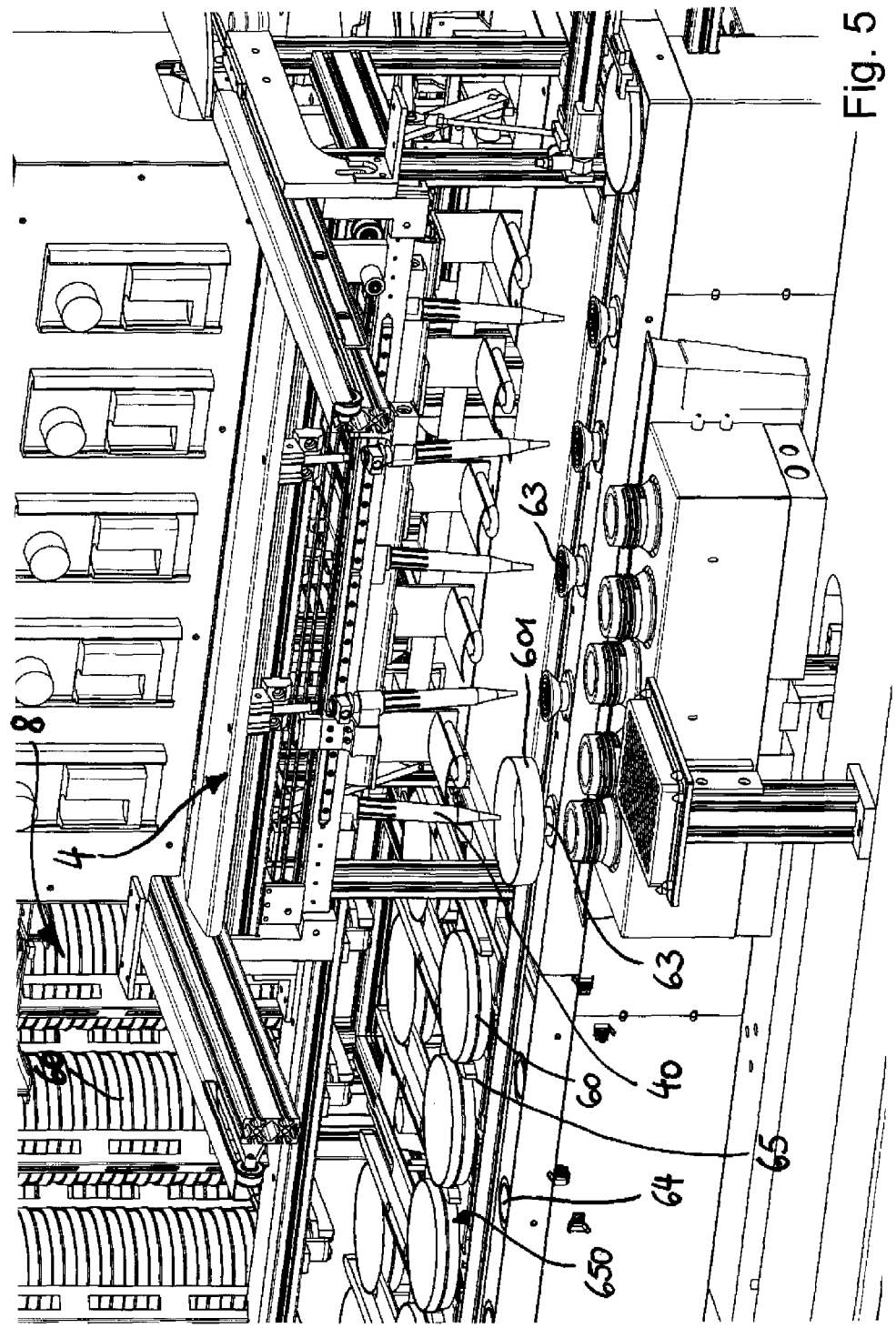
FIG. 5 shows a detail of the embodiment of the apparatus of FIG. 2 showing the pipettes in their dispensing position above the dishes in the dish support.

Next, as shown in FIG. 5, pipetting unit 4 with pipettes 40 is moved to a position in which the tips of the pipettes 40 are arranged centrally over the Petri-dishes 60 containing the pre-heated Agar disks 61. The mixtures contained in the pipettes 40 are then dispensed centrally onto the Agar disk. After that, the drives 63 spin the disks so that centrifugal forces act on the mixtures causing them to be forced towards the circumferentially running upstanding side wall 601 of the respective Petri-dish 60. After having spun the Petri-dishes for a predetermined amount of time, e.g. 1-2 seconds, spinning is stopped thus allowing a backflow of the dispensed mixture towards the center so as to form a uniform coating on the respective Agar disk. The lids 600 are then placed back onto the dishes with the aid of the suction cups 62 (see FIG. 3) so as to close the Petri-dishes again. The closed Petri-dishes 60 are then transported with the aid of suitable transport means towards a feed area which is capable of feeding the Petri-dishes 60 to the intermediate storage 8 in form of a rack.

The transport means may comprise two laterally arranged belts for moving the Petri-dishes 60 along dish support 6 (see FIG. 2) towards the left, lifting members 64, and transfer means 65. The transfer means 65 comprise bearing surfaces 650 on which the Petri-dishes 60 may come to rest.

The lifting members 64 lift the Petri-dishes 60 to the level of the transfer means 65 which move out at the left and right hand sides of the respective lifting members 64. The lifting members 64 are then lowered again so that the Petri-dishes 60 come to rest on the bearing surfaces 650 of the transfer means 65 which are then moved back again to their original position (FIG. 4). The next Petri-dishes 60 are collected in the same way whereby the formerly collected Petri-dishes 60 are shifted one position rearwards by the newcomer. This procedure is preferably repeated until the transfer means 65 hold the number of Petri-dishes 60 equivalent to the number of columns of rack 8.

The Petri-dishes 60 are introduced into rack 8 from below. Once rack 8 is completely filled with Petri-dishes 60 it can be forwarded to an incubator (not shown) for a predetermined amount of time (e.g. for two days) and under predetermined conditions (e.g. at a temperature of 37° C.) After that, the number of colonies of *salmonella* strains that have developed during the incubation time is counted, and based on that it is determined whether or not the substance and its metabolite have passed the Ames-test. Therefore, it is vital that for each substance to be tested the substance per se and potential metabolites thereof are subjected to the Ames-test. Once the dispensing of the substances contained in the pipettes 40 has been performed, pipetting unit 4 is moved back towards collecting pan 52. The pipettes 40 used are preferably disposable pipettes 40, so that after single use the used pipettes are inserted into collecting pan 52 and new ones are attached to the pipetting unit 4. The disposable pipettes 40 are preferably made from a suitable (inert) plastic material.

Figure 6:
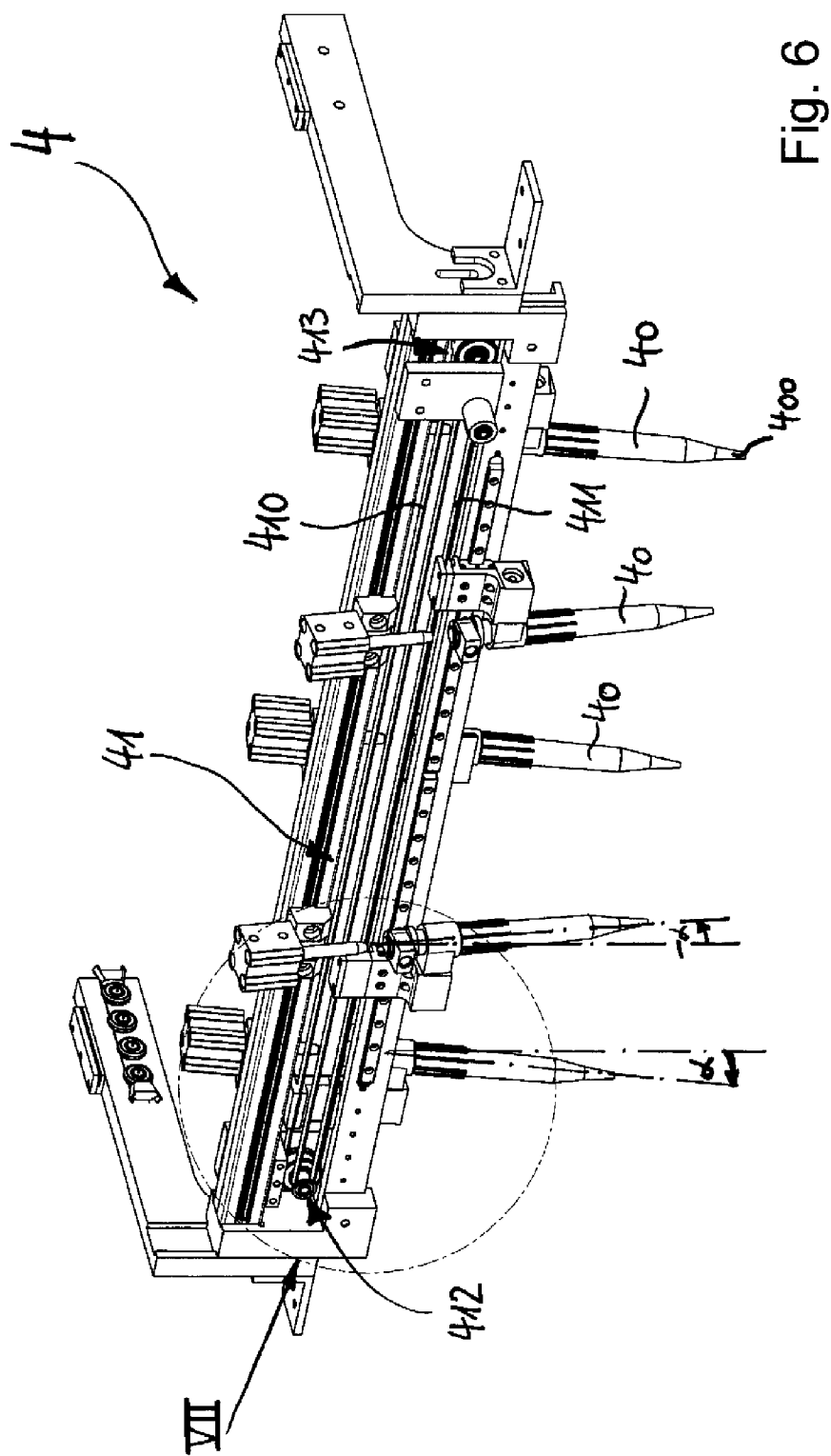
FIG. 6 shows the movable pipetting unit carrying the pipettes.

Pipetting unit 4 is shown in more detail in FIG. 6. It is clear from the description of the apparatus above, that at the time the pipettes 40 have to be introduced into the wells 10 of the micro-well plate 1 which are spaced from one another only at small distances, the standard pipettes could collide. Although the tips 400 of the pipettes only have a small diameter which can be easily inserted into the wells 10 the diameter of the pipettes then increases conically. To avoid collisions, the pipettes 40 are arranged at an inclination angle $\alpha$ relative to the normal to the plane of the plate support 3. Adjacently arranged pipettes 40 are arranged at opposite inclinations $\alpha$, $-\alpha$ so as to avoid collisions. The absolute value of the angle of inclination $\alpha$, $-\alpha$, respectively, is preferably within the range up to 10° relative to the normal, and may for example be 7.5°.

Figure 7:
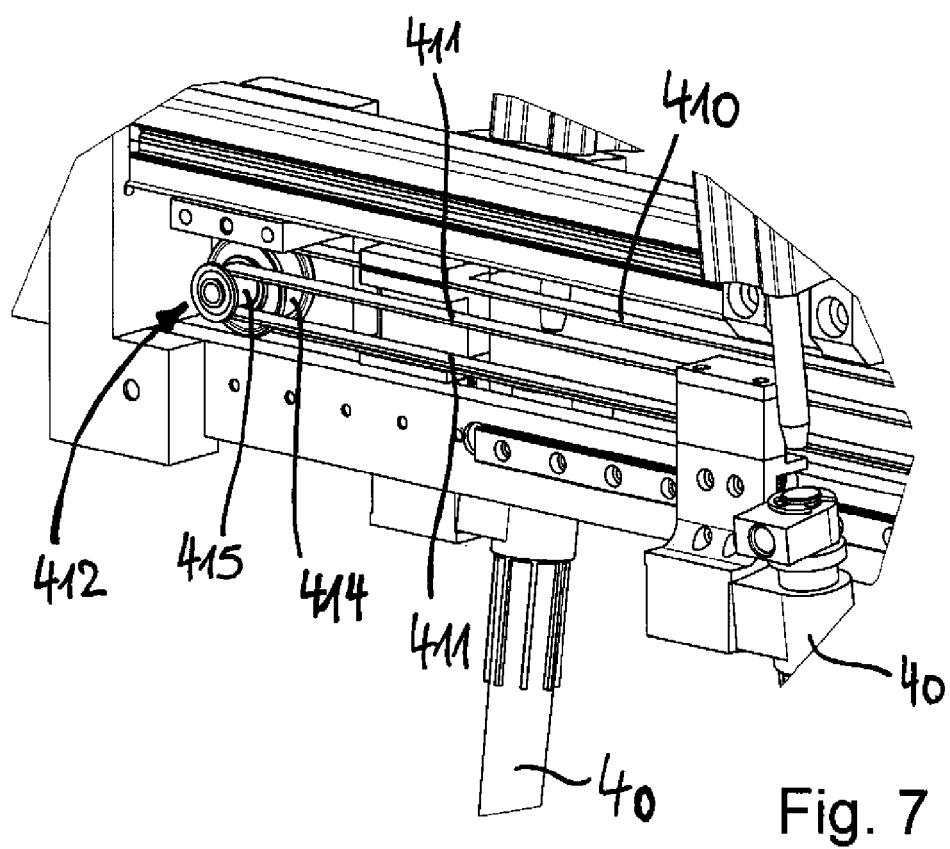
FIG. 7 shows a detail of the movable pipetting unit showing an embodiment of the gear with a fixed gear transmission ratio.

Also, as is clear from the description of the apparatus 2 while the pipettes 40 have to be arranged at a very small distance relative to one another as they are introduced into adjacently arranged wells 10 of the micro-well plate 1, they have to be moved away from one another so that they have a greater distance relative to one another when they have to be introduced into the containers 5, and they have to be moved still farther away from one another so as to be properly positioned above the respective open Petri-dishes 60. This movement of the pipettes 40 can be achieved with the aid of a spacing mechanism 41, an embodiment of which is shown in FIG. 6 and in an enlarged view in the detail VII shown in FIG. 7. The spacing mechanism 41 comprises two belts 410,411 which are engageably guided around two hubs 412,413, one of which can be electrically driven. Each hub 412,413 has two hub portions 414,415, respectively, one hub portion 414 having a larger diameter and the other hub portion 415 having a smaller diameter. The central one of the five pipettes 40 is not attached to any of the belts 410,411, while the two pipettes 40 immediately adjacent to the central pipette are attached to belt 411 which is guided around hub portion 415 having the smaller diameter, one pipette 40 being attached to the upper part of belt 411 and the other pipette 40 being attached to the lower part. Accordingly, depending on the direction in which belt 411 is moved, the pipettes 40 move towards or away from one another. Similar considerations apply for the outermost pipettes 40 which are both attached to belt 410 which is guided around hub portion 414 having the larger diameter, one of the pipettes 40 being attached to the upper part of belt 410 and the other one being attached to the lower part. By choosing the ratio of the diameters of the hub portions 413 and 414, a fixed gear transmission ratio can be achieved, e.g. 2:1, 3:1, or whatever.

Having described a specific embodiment of the apparatus and process according to the invention it is clear for the skilled person that various modifications can be made without departing from the general teaching of the invention. Therefore, the scope of protection is not intended to be limited to the described embodiments but rather is defined by the appended claims.

The invention claimed is:

1. An apparatus for the automatic testing of substances for potential carcinogenicity, comprising:
    at least one micro-well plate, the micro-well plate comprising a plurality of micro-wells including a plurality of substance/*salmonella* mixtures or substance/*salmonella*/liver enzymes mixtures therein;
    a plate support on which the at least one micro-well plate is placed;
    a movable pipetting unit comprising a plurality of pipettes,
        wherein the pipettes of the plurality of pipettes of the moveable pipetting unit are arranged at an inclination angle relative to a normal to the plane of the plate support,
        wherein adjacently arranged pipettes of the plurality of pipettes are arranged at inclined opposite angles relative to the normal, and
        wherein the inclination angle is in the range up to 10° relative to the normal, and about 7.5° relative to the normal;
    a plurality of containers containing a liquid culture medium, the plurality of containers corresponding to the plurality of pipettes of the pipetting unit;
    a dish support on which a plurality of dishes corresponding to the plurality of pipettes is arranged, each dish of the plurality of dishes having a bottom and an upstanding side wall surrounding the bottom as well as a solid culture medium arranged on the bottom of the dish;
    a plurality of spinners corresponding to the plurality of dishes arranged on the dish support, the plurality of spinners configured to spin the dishes to generate centrifugal forces;
    a plurality of suction cups corresponding to the plurality of dishes arranged on the dish support for placing a lid on each of the dishes so as to close the respective dishes; and
    a plurality of laterally arranged belts for transporting the closed dishes to an intermediate storage capable of collecting a plurality of closed dishes so as to forward them to an incubator.

2. The apparatus according to claim 1, further comprising a plurality of IR-heaters corresponding to the plurality of dishes arranged on the dish support, the IR-heaters configured to be positioned above the respective solid culture medium arranged in the respective dishes on the dish support.

3. The apparatus according to claim 1, wherein the pipetting unit comprises a gear configured to laterally move the pipettes towards and away from one another.

4. The apparatus according to claim 3, wherein the gear is configured with a fixed gear transmission ratio.

5. The apparatus according to claim 1, wherein the pipettes are disposable pipettes.

* * * * *